US00PP10752P

United States Patent [19]

VandenBerg

[11] Patent Number: Plant 10,752

[45] Date of Patent: Jan. 12, 1999

[54] CHRYSANTHEMUM PLANT NAMED 'CORAL SUERTE'

[75] Inventor: Cornelis P. VandenBerg, Salinas, Calif.

[73] Assignee: Yoder Brothers, Inc., Barberton, Ohio

[21] Appl. No.: 867,696

[22] Filed: Jun. 2, 1997

[51] Int. Cl.[6] ..... A01H 5/00

[52] U.S. Cl. ..... Plt./74.1

[58] Field of Search ..... Plt./74.1, 82.4

[56] References Cited

U.S. PATENT DOCUMENTS

| | | | |
|---|---|---|---|
| P.P. 10,225 | 2/1998 | VandenBerg | Plt./74.1 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using x–and gamma radiation", Euphytica, 15:204–210.

*Primary Examiner*—Howard J. Locker
*Attorney, Agent, or Firm*—C. A. Whealy

[57] ABSTRACT

A distinct cultivar of Chrysanthemum plant named 'Coral Suerte', characterized by its daisy-type inflorescences that are about 10 cm in diameter; attractive coral ray florets and bright yellow disc florets; numerous ray florets per inflorescence arranged in multiple rows; numerous disc florets per inflorescence; and excellent postproduction longevity with flowering stems maintaining good substance and color for about three to four weeks in an interior environment after one week of cool storage.

3 Drawing Sheets

The present invention relates to a new and distinct cultivar of chrysanthemum plant, botanically known as *Dendranthema grandiflora* and referred to by the cultivar name Coral Suerte.

The new cultivar is a product of a mutation induction breeding program conducted by the inventor in Fort Myers, Fla., and Salinas, Calif. The objective of the program is to create new Chrysanthemum cultivars having inflorescences with desirable form and floret colors, good substance, and excellent post-production longevity.

The new cultivar originated by exposing unrooted cuttings of the Chrysanthemum cultivar 'Suerte' (disclosed in U.S. Plant Pat. No. 10,225) to a X-ray radiation level of 1,750 rads on Oct. 13, 1994 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar 'Coral Suerte' was discovered and selected by the inventor as a single flowering plant within this population on Sep. 20, 1995. The selection of this plant was based on its desirable inflorescence form and floret colors, good substance, and excellent post-production longevity.

In side-by-side comparisons conducted in Salinas, Calif., plants of the new Chrysanthemum differ from plants of the parent cultivar, 'Suerte', in ray floret color as plants of 'Suerte' have dark pink/purple-colored ray florets. Additionally plants of the new Chrysanthemum have stems that are about 15 cm shorter than plants of 'Suerte.' In side-by-side comparisons conducted in Salinas, Calif., plants of the new Chrysanthemum have also been compared to other similar cultivars such as 'Regal Suerte' (disclosed in U.S. Plant patent application Ser. No. 08/867,698) and 'Orange Suerte'

(disclosed in U.S. Plant patent application Ser. No. 08/867,697). Plants of these cultivars also differ from plants of the new Chrysanthemum in ray floret color as plants of 'Regal Suerte' have dark purple-colored ray florets and plants of Orange Suerte have bright orange-colored ray florets. Additionally plants of the new Chrysanthemum have stems that are about 15 cm shorter than plants of 'Regal Suerte' or 'Orange Suerte.'

Asexual reproduction of the new cultivar by terminal cuttings taken in a controlled environment in Salinas, Calif., has shown that the unique features of this new Chrysanthemum are stable and reproduced true to type in successive generations.

The cultivar 'Coral Suerte' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Coral Suerte'. These characteristics in combination distinguish 'Coral Suerte' as a new and distinct cultivar:

1. Daisy-type inflorescences that are about 10 cm in diameter.
2. Attractive coral ray florets and bright yellow disc florets.
3. Numerous ray florets per inflorescence arranged in multiple rows.
4. Numerous disc florets per inflorescence.
5. Excellent postproduction longevity with flowering stems maintaining good substance and color for about three to four weeks in an interior environment after one week of cool storage.

The accompanying colored photographs illustrate the overall appearance of the new cultivar, showing the colors as true as it is reasonably possible to obtain in colored reproductions of this type.

The first photograph comprises a side perspective view of a typical flowering stem of 'Coral Suerte' grown as a single-stem spray cut Chrysanthemum.

The second photograph comprises a side perspective view of typical inflorescences of the cultivar Coral Suerte.

The third photograph comprises a top perspective view of upper (top) and lower (bottom) surfaces of typical inflorescences of the cultivars Suerte (left) and Coral Suerte (right) which shows the difference in ray floret colors.

The fourth photograph comprises a top perspective view of the upper surfaces of typical leaves of the cultivar Coral Suerte at two different stages of development.

Floret and foliage colors in the photogaphs may differ from the actual colors due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse. Day and night temperatures ranged from 18° to 24° C. and 16° to 17° C., respectively, and light levels ranged from 2,500 to 3,500 foot-candles. Rooted cuttings were planted Feb. 13, 1997 and cut flowers were harvested on Apr. 21, 1997. After planting rooted cuttings of the new cultivar, plants received two weeks of long day/short nights following by short day/long nights until flowering. Plants were grown as single-stem, that is, without pinching. Measurements and numerical values represent averages for six typical flowering stems.

Botanical classification: *Dendranthema grandiflora* cultivar 'Coral Suerte.'

Commercial classification: Daisy spray-type cut Chrysanthemum.

Parentage: Induced mutation of *Dendranthema grandiflora* cultivar Suerte (U.S. Plant Pat. No. 10,225).

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous daisy spray-type cut flower. Stems upright, uniform habit and freely branching.

*Flowering stem length.*—About 79 cm. Generally shorter than plants of the cultivar 'Suerte', 'Regal Suerte' and 'Orange Suerte.'

*Foliage description.*—Leaf arrangement: Alternate. Leaf size, fully expanded: Length: About 10.5 cm. Width: About 8 cm. Leaf apex: Cuspidate. Leaf base: Attenuate. Leaf margin: Deeply lobed. Leaf texture: Upper and lower surfaces slightly pubescent. Veins prominent on lower surface. Color: Young foliage upper surface: 147A. Young foliage lower surface: 147B. Mature foliage upper surface: 147A. Mature foliage lower surface: 147B. Venation upper surface: 147B. Venation lower surface: 147B. Petiole: Length: About 2.5 cm. Color: 147B.

Flowering description:

*Appearance.*—Daisy-type inflorescence form. Inflorescences borne on terminals, arising from leaf axils. Disc and ray florets arranged acropetally on a receptacle.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 52 days later.

*Postproduction longevity.*—In an interior environment, flowering stems will maintain good color and substance for about three or four weeks in an interior environment after one week of cool storage.

*Quantity of inflorescences.*—About 11 inflorescences per flowering stem.

*Inflorescence size.*—Diameter: About 10 cm. Depth (height): About 1.2 cm. Diameter of disc: About 1.75 cm. Diameter of receptacle: About 7 mm.

*Ray florets.*—Shape: Oblong. Size: Length: About 4.75 cm. Width: About 1.2 cm. Apex: Rounded to dentate. Base: Attenuate. Margin: Entire. Texture: Satiny, smooth, glabrous. Aspect: Flat. Number of ray florets per inflorescence: About 75. Color: When opening: Upper surface: 181C with purple overtones. Lower surface: 161B. Base: 154A. Mature: Upper surface: 181C/180D with purple overtones. Lower surface: 161B. Base: 154A.

*Disc florets:*—Shape: Tubular. Size: Length: About 8 mm. Width: Apex: About 2 mm. Base: About 1 mm. Number of disc florets per inflorescence: About 125. Color: Immature: 154A. Mature: Apex: 9A. Base: Greenish white. Throat: 9A.

*Peduncle.*—Aspect: Strong and angled about 50° to the stem. Length: First peduncle: About 9 cm. Fourth peduncle: About 13 cm. Seventh peduncle: About 18 cm. Texture: Pubescent. Color: 147B.

*Reproductive organs.*—Androecium: Present on disc florets only. Anther color: 15A. Pollen: Moderate, 15A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Coral Suerte', as illustrated and described.

* * * * *

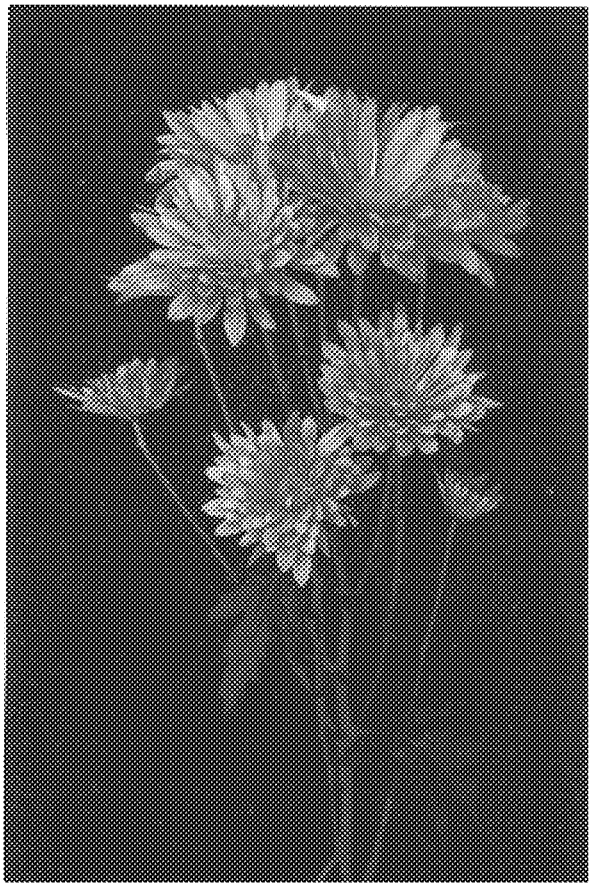

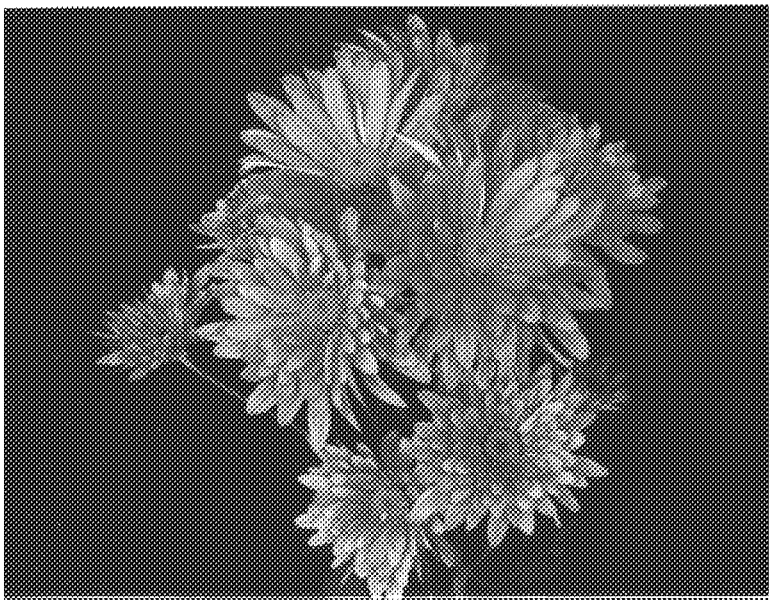

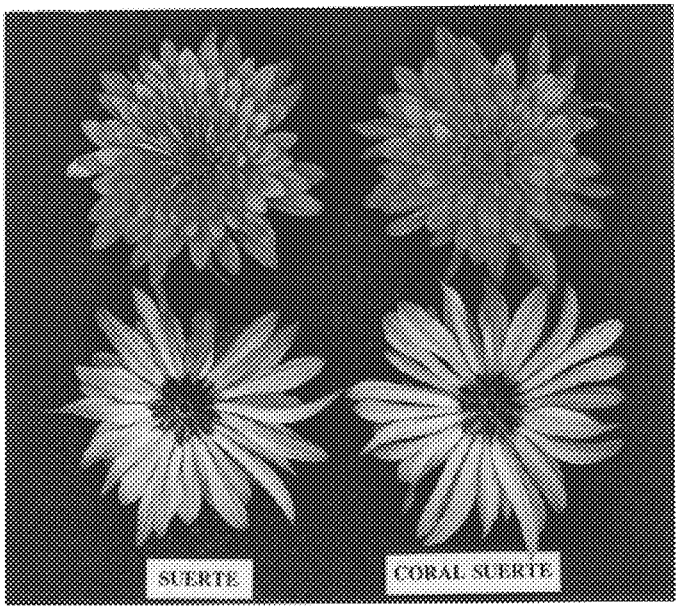
SUERTE
CORAL SUERTE
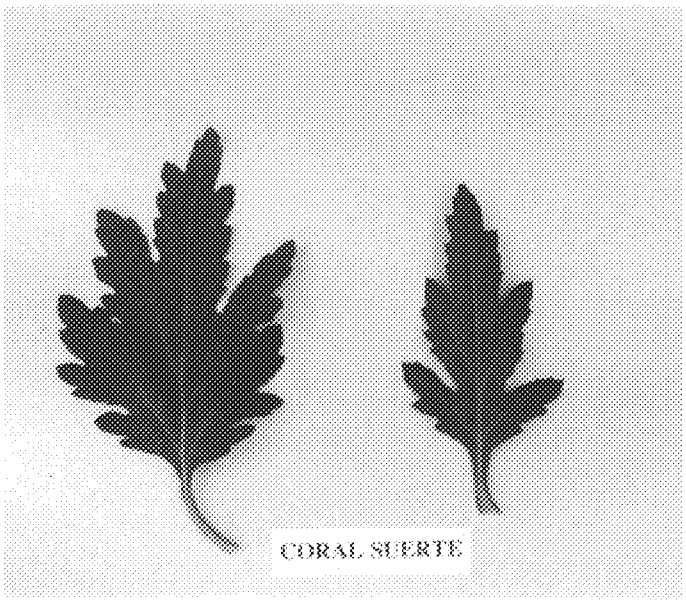
CORAL SUERTE